United States Patent
Scheuing et al.

(10) Patent No.: US 10,156,492 B2
(45) Date of Patent: Dec. 18, 2018

(54) METHOD FOR DETECTING WHEEL IMBALANCES IN A VEHICLE

(71) Applicant: Robert Bosch GmbH, Stuttgart (DE)

(72) Inventors: Jan Scheuing, Brackenheim (DE); Uwe Martin, Markgroeningen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 15/554,672

(22) PCT Filed: Jan. 15, 2016

(86) PCT No.: PCT/EP2016/050750
§ 371 (c)(1),
(2) Date: Aug. 30, 2017

(87) PCT Pub. No.: WO2016/142082
PCT Pub. Date: Sep. 15, 2016

(65) Prior Publication Data
US 2018/0038761 A1    Feb. 8, 2018

(30) Foreign Application Priority Data
Mar. 6, 2015 (DE) .......... 10 2015 204 115

(51) Int. Cl.
*G01M 1/22* (2006.01)
*G01M 1/28* (2006.01)
*G01M 17/013* (2006.01)

(52) U.S. Cl.
CPC .............. *G01M 1/225* (2013.01); *G01M 1/28* (2013.01); *G01M 17/013* (2013.01); *A61B 2562/0219* (2013.01)

(58) Field of Classification Search
None
See application file for complete search history.

(56) References Cited

U.S. PATENT DOCUMENTS

| 6,278,361 | B1* | 8/2001 | Magiawala | B60C 23/0408 340/438 |
|---|---|---|---|---|
| 2008/0086248 | A1* | 4/2008 | Lu | B60T 8/171 701/41 |
| 2008/0140278 | A1* | 6/2008 | Breed | G06F 8/65 701/31.4 |
| 2009/0139327 | A1* | 6/2009 | Dagh | G01M 1/225 73/457 |
| 2015/0210310 | A1* | 7/2015 | Akatsuka | B62D 5/04 701/41 |

FOREIGN PATENT DOCUMENTS

| DE | 102007052751 A1 | 5/2009 |
| DE | 102008064261 A1 | 9/2009 |
| WO | 2009070067 A1 | 6/2009 |

OTHER PUBLICATIONS

International Search Report for PCT/EP2016/050750, dated Apr. 20, 2016.

* cited by examiner

*Primary Examiner* — Leon Viet Q Nguyen
(74) *Attorney, Agent, or Firm* — Norton Rose Fulbright US LLP; Gerard Messina

(57) ABSTRACT

In a method for detecting wheel imbalances in a vehicle, the profile of the driving state variable is ascertained by sensor over a speed range of the vehicle; a frequency analysis is performed; and a resonance step-up is indicative of a wheel imbalance.

14 Claims, 2 Drawing Sheets

METHOD FOR DETECTING WHEEL IMBALANCES IN A VEHICLE

FIELD OF THE INVENTION

The present invention relates to a method for detecting wheel imbalances in a vehicle.

BACKGROUND INFORMATION

At higher speed ranges, wheel imbalances in vehicles that arise due to worn-out or damaged tires, for example, lead to vibrations that adversely affect vehicle safety and ride comfort. Over the long term, wheel imbalances can lead to secondary damage to the wheel suspension or the steering.

SUMMARY OF THE INVENTION

It is an object of the present invention to employ simple measures to detect wheel imbalances in a vehicle.

This objective is achieved in accordance with the present invention by the features described herein. The further descriptions herein disclose further embodiments.

The method for detecting wheel imbalances is used in vehicles, in particular in engine-driven vehicles, which may be in motor vehicles, trucks or motorcycles. Employing the method according to the present invention makes it possible to ascertain wheel imbalances on the basis of a driving state variable in the vehicle ascertained by sensor. Thus, it suffices to ascertain at least one driving state variable that undergoes an analysis from which a potential imbalance may be recognized.

This procedure has the advantage that the signals of a sensor system installed in the vehicle may be used, and no additional sensors are needed for detecting the imbalance.

The precondition for ascertaining the wheel imbalance is the sensor detecting the observed driving state variable over a defined speed range of the vehicle. The driving state variable should not merely be considered during a constant speed of the vehicle; rather, the vehicle must move within a minimum speed range of between 0 and an upper speed-limiting value, for example. The upper speed-limiting value represents a minimum speed that the vehicle must have reached in order for a wheel imbalance to be recognized precisely enough during analysis of the sensor-detected driving state variable. The speed-limiting value ensures that the driving state variable covers a characteristic speed range that also includes potential resonance frequencies in the vehicle.

The test performed to detect the wheel imbalances is based on a speed-dependent frequency analysis of the driving state variable. In the speed-dependent frequency analysis, resonance step-ups may be recognized from which a wheel imbalance may be inferred. It is useful to specify a limiting value for the resonance step-up upon whose reaching, a significant wheel imbalance exists; whereas below the limiting value, there is no wheel imbalance, or the wheel imbalances still vary within a tolerance range.

In principle, a driving state variable is considered to be any state variable of longitudinal, transversal or vertical dynamics, in particular speed and acceleration variables. It suffices to analyze exactly one driving state variable as a function of the frequency analysis to be able to infer a wheel imbalance in the case of a high enough resonance step-up.

The driving state variable under consideration is to be determined, in particular, via a standard sensor system installed in the vehicle. For example, a driving state variable for longitudinal, transversal or vertical dynamics may be detected via the sensor system of an electronic stability program (ESP) in the vehicle. Here, it may be the wheel speeds of at least one wheel of the vehicle.

If there is no imbalance in the wheel, or if the imbalance only has a small value, the profile of the driving state variable generally does not show any or only shows a relatively low resonance step-up in the frequency analysis as a function of the speed range under consideration. If the resonance step-up lies below a limiting value, no imbalance or only a slight imbalance may be inferred. On the other hand, if the resonance step-up reaches the limiting value, there is a significant imbalance. In such a case, a warning signal is advantageously generated that may acoustically, optically, and/or haptically notify the driver in the vehicle and/or be wirelessly transmitted to the outside.

In the latter case, the warning signal is wirelessly transmitted from the vehicle to an external reception point located outside of the vehicle where the warning signal is further processed. The reception point may be a repair shop, for example, where the warning signal may be used for contacting the vehicle owner and for planning a workshop visit. However, the vehicle manufacturer or a fleet manager may also be considered, inter alia, as a reception point.

The warning signal is transmitted externally to the reception point either via a communication device that is permanently installed in the vehicle, and/or via an external device, such as a smart phone, for example, that may be connected in the vehicle either via a cable or wirelessly, via Bluetooth, for example, and that communicates with a control unit or control device in the vehicle. The method for detecting wheel imbalances is advantageously carried out in this control unit or control device. The control unit or control device is one that is associated with the electronic stability program, for example.

Likewise possible, however, are control units or control devices that are independent of driver assistance systems or of vehicle units. In any case, the control unit or control device communicates with the sensor system that is installed in the vehicle and from whose sensor signals, the wheel imbalances may be ascertained via the frequency analysis. If no external device, such as a smart phone, is connected, the communication device installed in the vehicle communicates with the control unit or control device.

In principle, it suffices for the wheel imbalance to be determined in one wheel of the vehicle on the basis of the profile of the one detected driving state variable. One variant of an embodiment provides that the wheel imbalances be determined on the basis of the profile of at least two different driving state variables, for example, on the basis of the wheel speed profile and an acceleration variable. Considering at least one additional driving state variable enhances the fail-safety and the probability of reliably detecting an imbalance.

In principle, the method makes it possible for the wheel imbalances to be determined at each individual wheel of the vehicle. For this purpose, the wheel speed is advantageously analyzed at every wheel in question.

The method may be carried out in a control unit or control device during a drive of the vehicle. If an imbalance is recognized, the warning signal generated in response thereto may also be stored and signaled again during a later drive and/or transmitted to an external reception point.

Further advantages and useful embodiments are to be inferred from the further claims, the description of the figures, and the drawings.

DETAILED DESCRIPTION

Figure 1:
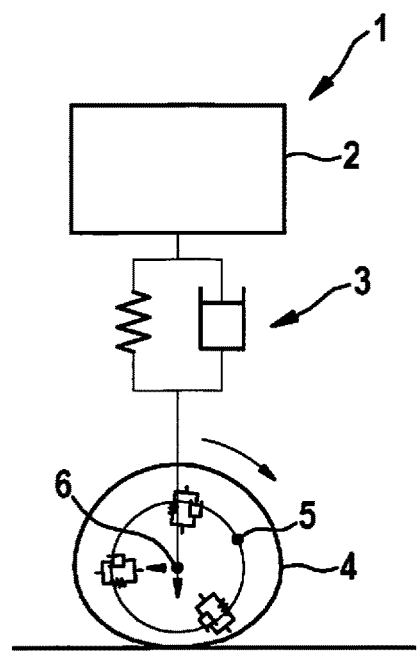
FIG. 1 schematically shows a simple abstract model of a vehicle having a vehicle wheel that has a wheel imbalance.

The abstract system for a vehicle 1 as shown in FIG. 1 includes an automotive body 2, a suspension/shock-absorber system 3, as well as a wheel 4 that is coupled via suspension/shock-absorber system 3 to body 2. Wheel 4 has an imbalance 5 that is symbolically marked as a circle therein. Both static, as well as dynamic imbalances are possible. Imbalance 5 may be in the form of a missing or an additional weight or be caused by a lasting deformation of the wheel.

Vehicle 1 has a sensor system having a wheel-speed sensor 6 for ascertaining the speeds of wheel 4. The sensor system is part of an electronic stability program (ESP) in the vehicle and, in addition to wheel-speed sensor 6, may include further sensors for ascertaining the longitudinal, transversal and/or vertical dynamics of the vehicle. However, the sensor system may also be configured independently of an electronic stability program. A wheel-speed sensor 6 is advantageously associated with each wheel 4 of the vehicle.

Figure 2:
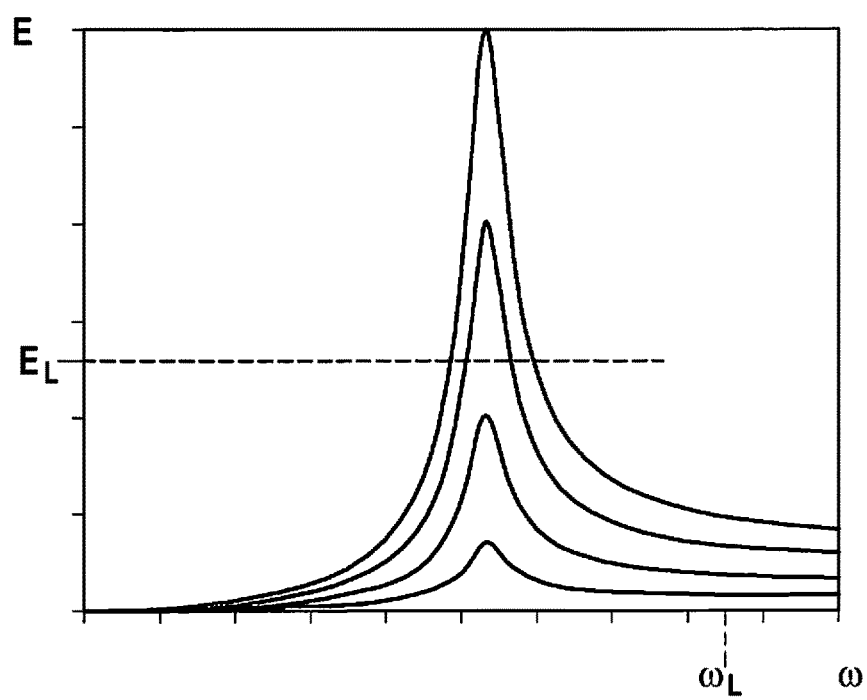
FIG. 2 is a diagram showing a speed-dependent frequency analysis of the wheel-speed profile of the vehicle wheel having varying degrees of wheel imbalance in the region of a resonance step-up.

FIG. 2 is a diagram showing the frequency analysis of various wheel-speed profiles. The profile of wheel speeds $\omega$ is shown in rad/s between 0 and a maximum speed value along the X-axis. The frequency is analyzed once the vehicle has driven through a speed range of at least up to a speed-limiting value of $\omega_L$, and the wheel speeds have been continuously recorded during this time. Speed-limiting value $\omega_L$ is selected to reflect the exceedance of a resonant frequency in the vehicle wheel, so that the recorded speed profile also covers the range that includes resonant frequencies.

Plotted in the diagram in accordance with FIG. 2 are altogether four wheel-speed profiles having resonance step-ups of different heights in the region of the resonant frequency. Shown along the Y-axis is energy content E or, alternatively, the amplitude. If the resonance step-up of a wheel-speed profile, shown in the frequency analysis, exceeds an associated limiting value $E_L$, then a significant imbalance in the wheel must be assumed. This is the case for the two higher wheel-speed profiles in the illustrated example, while the two lower wheel-speed profiles do not reach limiting value $E_L$, even in the region of the resonance step-up thereof.

By considering limiting value $E_L$, it is ensured that only a significant resonance step-up indicates an imbalance. If, on the other hand, the profiles lie below limiting value $E_L$, then either no imbalance or an acceptable imbalance is assumed that does not adversely affect the ride comfort or the driving safety.

Figure 3:
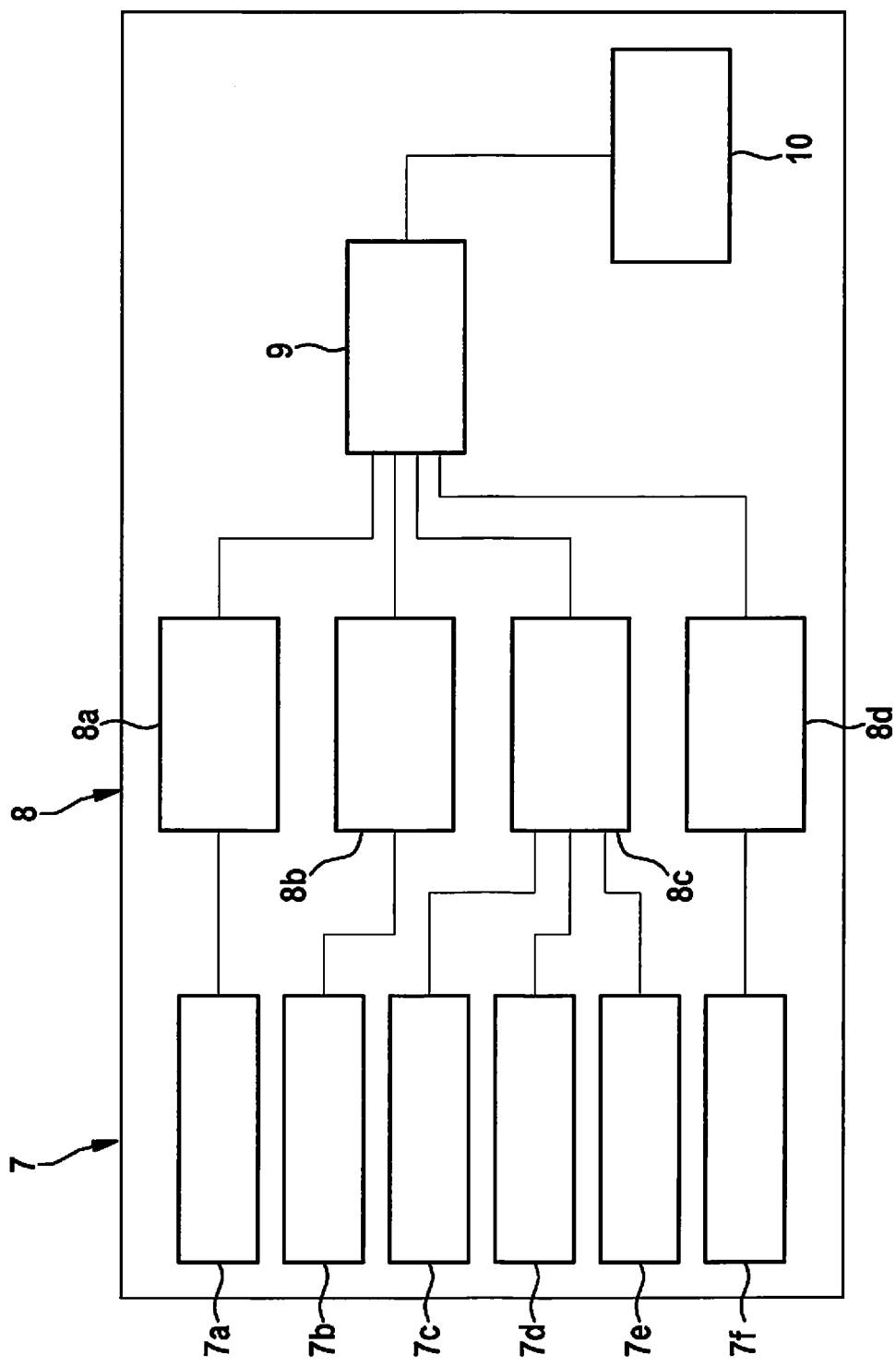
FIG. 3 is a block diagram for implementing the method for detecting wheel imbalances and for transmitting warning signals to an external reception point.

The block diagram according to FIG. 3 shows the method sequence for detecting wheel imbalances in the vehicle. Installed in the vehicle is a sensor system 7 that includes a plurality of different sensors 7a through 7f which are able to record driving state variables, inter alia the wheel speeds and vehicle accelerations, however, also other parameters in the vehicle, such as temperature, the electrical-system voltage, etc. Associated with each vehicle wheel is a speed sensor 7c, for example, which may be used to permanently ascertain the speed profile of the wheel in question.

The signals from the sensors are fed to various units and systems 8 in the vehicle; inter alia, to the control unit or control device 8c of an electronic stability program. The ascertained signals may be analyzed in the control unit or control device and be subject to a frequency analysis to detect wheel imbalances in accordance with FIG. 2. If the analysis reveals that a wheel imbalance is present, a warning signal is generated that may be signaled in a communication device 9 in the vehicle, in particular acoustically, optically or haptically.

Additionally or alternatively, the warning signal may be wirelessly transmitted to an external reception point, for example, to a repair shop. The transmission is carried out either directly via communication device 9 or via an external device 10, such as a smart phone, for example, that is connected to communication device 9 or that communicates wirelessly with the same.

What is claimed is:

1. A method comprising:
    ascertaining a driving state variable by a sensor over a speed range of a vehicle;
    performing a frequency analysis of the driving state variable, thereby obtaining for each of a plurality of speeds of the speed range a respective one of a plurality of frequency values;
    analyzing the plurality of frequency values to identify a step-up in the plurality of frequency values within the speed range;
    comparing a peak one of the frequency values of the identified step-up to a single threshold value applied to the plurality of speeds of the speed range; and
    determining whether there is a wheel imbalance of a wheel of the vehicle based on a result of the comparison.

2. The method of claim 1, wherein the sensor is part of a sensor system of an electronic stability program in the vehicle.

3. The method of claim 1, further comprising outputting a warning signal in response to the wheel imbalance being determined to be present in the determining step, wherein the wheel imbalance is determined to be present in the determining step when the peak one of the plurality of frequency values of the identified step-up exceeds the threshold value.

4. The method of claim 3, wherein the warning signal is signaled in the vehicle.

5. The method of claim 3, wherein the warning signal is wirelessly transmitted from the vehicle to a reception point outside of the vehicle.

6. The method of claim 5, wherein the warning signal is transmitted to the reception point via an external device that is connected in the vehicle.

7. The method of claim 1, wherein signals from at least one further sensor are evaluated to determine the imbalance.

8. The method of claim 1, wherein the frequency analysis is only performed if the vehicle speed reaches a speed-limiting value.

9. A control unit, comprising:
    a control device configured to perform the following:
       ascertain, based on output of a sensor, a driving state variable over a speed range of a vehicle;
       perform a frequency analysis of the driving state variable, thereby obtaining for each of a plurality of speeds of the speed range a respective one of a plurality of frequency values;
analyze the plurality of frequency values to identify a step-up in the plurality of frequency values within the speed range;
compare a peak one of the frequency values of the identified step-up to a single threshold value applied to the plurality of speeds of the speed range; and
determine whether there is a wheel imbalance of a wheel of the vehicle based on a result of the comparison.

10. A vehicle, comprising:
at least one wheel-speed sensor; and
a control device configured to perform the following:
  ascertain, based on output of the at least one sensor, a driving state variable over a speed range of a vehicle;
  perform a frequency analysis of the driving state variable, thereby obtaining for each of a plurality of speeds of the speed range a respective one of a plurality of frequency values;
  analyze the plurality of frequency values to identify a step-up in the plurality of frequency values within the speed range;
  compare a peak one of the frequency values of the identified step-up to a single threshold value applied to the plurality of speeds of the speed range; and
  determine whether there is a wheel imbalance of a wheel of the vehicle based on a result of the comparison.

11. The method of claim 3, wherein the warning signal is wirelessly transmitted from the vehicle to a reception point outside of the vehicle to a repair shop.

12. The method of claim 5, wherein the warning signal is transmitted to the reception point that is outside of the vehicle via a smart phone that is connected in the vehicle.

13. The method of claim 1, wherein signals, which are vehicle accelerations, from at least one further sensor are also evaluated to determine the imbalance.

14. The method of claim 1, wherein the speed range for the plurality of speeds of which the plurality of frequency values used for the determining are obtained is a predefined limited speed range, frequency values of the driving state variable corresponding to speeds out of the speed range being ignored in at least one of the ascertaining, performing, and analyzing steps.

* * * * *